United States Patent
Chez

(10) Patent No.: US 8,741,847 B2
(45) Date of Patent: Jun. 3, 2014

(54) AGENT AND METHODS FOR REDUCING INFLAMMATORY MARKERS

(76) Inventor: Michael Chez, Granite City, CA (US)

(*) Notice: Subject to any disclaimer, the term of this patent is extended or adjusted under 35 U.S.C. 154(b) by 0 days.

(21) Appl. No.: 13/463,851

(22) Filed: May 4, 2012

(65) Prior Publication Data

US 2012/0230986 A1    Sep. 13, 2012

Related U.S. Application Data

(63) Continuation-in-part of application No. PCT/US2010/055543, filed on Nov. 5, 2010.

(60) Provisional application No. 61/258,644, filed on Nov. 6, 2009.

(51) Int. Cl.
*A61K 38/00* (2006.01)
*C07K 16/00* (2006.01)

(52) U.S. Cl.
USPC ...... 514/17.5; 514/17.7; 514/21.3; 530/388.1

(58) Field of Classification Search
None
See application file for complete search history.

(56) References Cited

U.S. PATENT DOCUMENTS

| | | |
|---|---|---|
| 7,456,224 B2 * | 11/2008 | Chez .......................... 514/662 |
| 7,709,213 B2 | 5/2010 | Chez |
| 8,354,438 B2 | 1/2013 | Chez |
| 2006/0052428 A1 | 3/2006 | Chez |
| 2006/0079495 A1 | 4/2006 | Blum |
| 2006/0188505 A1 * | 8/2006 | Skurkovich et al. ....... 424/145.1 |
| 2008/0108643 A1 | 5/2008 | Chez |
| 2008/0269123 A1 | 10/2008 | Li et al. |
| 2008/0305551 A1 | 12/2008 | Chez |

OTHER PUBLICATIONS

Chez, M., et al., "Practical Treatment with Pulse Does Corticosteroids in Pervasive Developmental Delay or Autistic Patients with Abnormal Paitents with Abnormal Epileptiform Sleep EEG and Language Delay," 8th International Child Neurology Congress, Sep. 13-18, 1998, pp. 695-698.
Chez, M., et al., "Immunizations, Immunology, and Autism," Seminars in Pediatric Neurology, 2004, pp. 214-217.
Chez, M., et al., "Relationship of Epileptic Activity in Autism and Pervasive Developmental Disorder to Possible Autoimmune Encephalopathy," The Journal of Developmental and Learning Disorders, 1999, pp. 118-125, issue 2.
Chez, M., et al., "Neurologic Treatment Strategies in Autism: An Overview of Medical Intervention Strategies," Seminars in Pediatric Neurology, 2004, pp. 229-235.
Chez, M., et al., "Immune Therapy in Autism: Historical Experience and Future Directions with Immunomodulatory Therapy," Neurotherapeutics: The Journal of the American Society for Experimental NeuroTherapeutics, Jul. 2010, pp. 293-301, vol. 7.
Connolly A., et al., "Brain-Derived Neurotrophic Factor and Autoantibodies to Neural Antigens in Sera of Children with Autistic Spectrum Disorders, Landau-Kleffner Syndrome, and Epilepsy," Society of Biological Psychiatry, 2005.
Chez, M., et al., "Chapter VI: Carnosine in Autistic Spectrum Disorders," Focus on Autism Research, Dec. 9, 2004, pp. 153-162.
Zimmerman, A. W., et al., "Cerebrospinal Fluid and Serum Markers of Inflammation in Autism," Pediatric Neurology, 2005, pp. 195-201, vol. 33 No. 3.
Vargas, D. L., et al., "Neuroglial Activation and Neuroinflammation in the Brain of Patients with Autism," American Neurological Association, 2004, pp. 67-81, vol. 57, No. 1.
Chez, MD, Michael G., et al. "Double-Blind, Placebo-Controlled Study of L-Carnosine Supplementation in Children with Autistic Spectrum Disorder", Journal of Child Neurology, 2002, pp. 833-37, vol. 17, No. 11.
Connolly AM, et al., "Serum Autoantibodies to Brain in Landau-Kleffner Variant, Autism and Other Neurologic Disorders," J. Pediatr 1999; 134:607-13.
Chez, M., et al., "Clinical Inflammatory Markers in CSF of Autistic Children with Regression," Annals of Neurology, Sep. 2006, vol. 60 (suppl 3), p. S68-S69.
Chez, M. G., et al., "Elevation of Tumor Necrosis Factor-Alpha in Cerebrospinal Fluid of Autistic Children," Pediatric Neurology, Jun. 2007, pp. 361-365, vol. 36 No. 6.
Chez, M. G., et al., "Frequency of eplieptiform EEG abnormalities in a sequential screening of autistic patients with no known clinical epilepsy from 1996 to 2005," Epilepsy & Behavior, 2006.
International Search Report and Written Opinion in PCT Application PCT/US10/55543, dated Jan. 2011.

* cited by examiner

*Primary Examiner* — Olga N Chernyshev
(74) *Attorney, Agent, or Firm* — Cahn & Samuels, LLP

(57) ABSTRACT

A method for treating an autism spectrum condition includes administering an effective dose of a TNF-α inhibiting agent to a person having an autism spectrum condition or pervasive development disorder and at least one of elevated TNF-α in the cerebrospinal fluid or elevated TNF-α in the serum, as compared to normal conditions; and lowering at least one of the elevated TNF-α in the cerebrospinal fluid or elevated TNF-α in the serum. A TNF-α inhibiting agent includes at least one of Lenalinomide; Thalidomide; L-Carnosine; Infliximab; Etanercept; a stem cell preparation; derivatives thereof, isomers thereof, or pharmaceutically acceptable salts thereof.

11 Claims, 5 Drawing Sheets

• TNF-alpha

Clinical Global Impression

• Neuropsychological Testing

AGENT AND METHODS FOR REDUCING INFLAMMATORY MARKERS

This application is a Continuation-In-Part application of PCT international application PCT/US2010/055543 filed on Nov. 5, 2010, which claims priority to U.S. provisional application 61/258,644, filed on Nov. 6, 2009 in the U.S. Patent and Trademark Office, the entireties of which are incorporated by reference herein.

TECHNICAL FIELD

The present invention is directed to using agents such as medications or stem cell preparations to reduce inflammatory markers in autism or pervasive developmental disorder patients having cerebrospinal fluid (CSF) and/or serum markers of cytokine inflammatory responses and to treat other related autoimmune findings.

The present invention identifies agents that are not previously used in autism spectrum conditions. In specific embodiments, the mechanism of the present invention involves cytokine ratios in cerebrospinal fluid (CSF) to serum levels, such as tumor necrosis factor alpha (TNF-$\alpha$), which are elevated in cases of autism with regression. The mechanism may also involve elevated CSF and/or serum levels above normal values for tumor necrosis factor alpha and other pro-inflammatory cytokines such as interleukin-1 beta (IL-$\beta$).

BACKGROUND

Autism with regression may represent 30-40% of autism cases. Also, more cases may exist with potential cytokine disturbances representing a chronic dysfunctional inflammatory pattern.

In utero exposure to a maternal inflammatory disease state may predispose some patients with autism to have elevated pro-inflammatory state with elevated cytokine profiles affecting developmental outcomes. Modification of autism course may be possible by treatment of these elevated markers and effectively normalizing the pro-inflammatory state.

SUMMARY OF INVENTION

A method for treating an autism spectrum condition is provided that includes administering an effective dose of a TNF-$\alpha$ inhibiting agent to a person having an autism spectrum condition or pervasive development disorder and at least one of elevated TNF-$\alpha$ in the cerebrospinal fluid or elevated TNF-$\alpha$ in the serum, as compared to normal conditions; and lowering at least one of the elevated TNF-$\alpha$ in the cerebrospinal fluid or elevated TNF-$\alpha$ in the serum.

According to another aspect of the present invention, a method is provided in which an effective dose of a TNF-$\alpha$ inhibiting agent is administered to a person having an elevated ratio of TNF-$\alpha$ in the cerebrospinal fluid to TNF-$\alpha$ in serum, as compared to normal conditions; and the elevated ratio of TNF-$\alpha$ in the cerebrospinal fluid to TNF-$\alpha$ in the serum is lowered.

According to yet another aspect of the present invention, a TNF-$\alpha$ inhibiting agent is provided for lowering at least one of the elevated TNF-$\alpha$ in the cerebrospinal fluid or elevated TNF-$\alpha$ in the serum. The TNF-$\alpha$ inhibiting agent includes at least one of the following agents: Lenalinomide; Thalidomide; L-Carnosine; Infliximab; Etanercept; a stem cell preparation; derivatives thereof, isomers thereof, or pharmaceutically acceptable salts thereof.

As used herein "substantially", "generally", "relatively", "approximately", and "about" are relative modifiers intended to indicate permissible variation from the characteristic so modified. It is not intended to be limited to the absolute value or characteristic which it modifies but rather approaching or approximating such a physical or functional characteristic.

References to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

In the following description, reference is made to the accompanying drawings, which are shown by way of illustration to specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF INVENTION

Figure 1B:
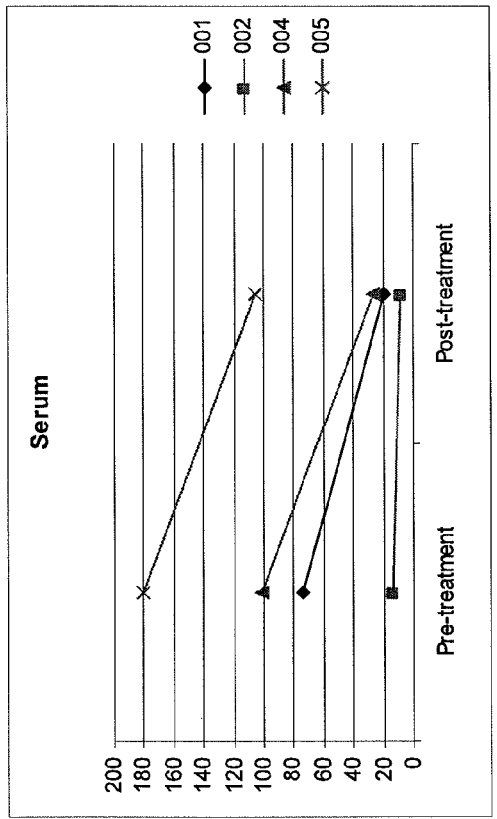
FIGS. 1a and 1b are graphs of TNF-$\alpha$ levels in CSF and serum before and after treatment with lenalinomide.

In autism spectrum cases, TNF-$\alpha$ elevation in at least one of CSF or serum, or disturbances shown by elevated ratio of TNF-$\alpha$ levels in CSF vs. TNF-$\alpha$ levels in serum, have a potential treatment response using TNF-$\alpha$ inhibitors, which may alter a chronic inflammatory process.

In specific embodiments, the basis for this observation includes clinically relevant responses noted in autism spectrum patients that are treated clinically with TNF-$\alpha$ inhibiting agents or immune modifying stem cell preparations.

Treatment of autism spectrum conditions including, but not limited to, pervasive development disorder (PDD-NOS), Autism, and Asperger's, is based on inhibition of TNF-$\alpha$ elevation and may also include inhibition of other pro-inflammatory cytokines such as Interleuken-$\beta$.

According to the present invention, agents for reducing inflammatory markers such as TNF-$\alpha$ comprise at least one of Lenalinomide (REVLIMID®); Thalidomide; L-Carnosine; Tumeric, Cat's Claw, Infliximab (REMICADE®); Etanercept (ENBREL® or Embrel); a stem cell preparation aimed at modulating immune regulation of cytokines or pre-inflammatory state; derivatives thereof, isomers thereof, or pharmaceutically acceptable salts thereof.

The agent for reducing inflammatory markers may be in the form of an oral administration (e.g., tablet) or an injectable administration. In specific embodiments, these agents may be dietary supplements with anti-inflammatory properties which, among other mechanisms, particularly lower TNF-α levels.

According a specific embodiment of the present invention, treatment of an autism spectrum condition comprises administering an effective dose of at least one such agent to a person having an autism spectrum condition and at least one of elevated TNF-α in the cerebrospinal fluid or elevated TNF-α in the serum, as compared to normal conditions and lowering at least one of the elevated TNF-α in the cerebrospinal fluid or elevated TNF-α in the serum.

A. Lenalinomide

Lenalinomide (REVLIMID®) or derivatives thereof have shown a lowering of CSF and serum ratios of TNF-α and other inflammatory cytokines when TNF-α is elevated in an inflammatory response.

In specific embodiments, test subjects or patients were males 6 to 16 years of age who had been diagnosed with autistic spectrum disorder as defined by DSM-IV criteria. The subjects had inflammatory CSF and serum markers with an elevated level of TNF-α (for example, greater than 50 pg/ml) or other cytokine markers such as IL-1, IL-6 or MECP-1, or serum levels of such cytokines greater than two times (2×) normal levels even in absence of CSF markers. Alternatively, the patients may have interictal epiliptiform EEG changes in the absence of clinical seizures, if CSF inflammatory markers are identified.

Baseline laboratory test results were within normal range for age for at least one of serum creatinine, total bilirubin, AST, ALT, absolute neutrophil count, or platelet count.

Patients excluded from treatments or tests included those patients with (1) any serious medical condition, laboratory abnormality, genetic, brain, structural, or psychiatric illness that would prevent the subject from participating; (2) a history of neutropenia, thrombocytopenia or other types of myelosuppression or risk factors for myelosuppression; (3) a history or risk factors for thromboembolic events; or (4) any condition, including the presence of laboratory abnormalities, which places the subject at unacceptable risk if he/she were to participate in the study or confounds the ability to interpret data from the study.

Also excluded are those patients with (1) use of any other experimental drug or therapy within 28 days of baseline; (2) current use of steroids (e.g. dexamethasone, prednisone), anthracyclines (Doxil, Adriamycin); (3) known hypersensitivity to thalidomide; (4) the development of erythema nodosum if characterized by a desquamating rash while taking thalidomide or similar drugs; (5) any prior use of lenalinomide; or (6) known positive for HIV or infectious hepatitis, type A, B or C or tuberculosis.

In specific embodiments, serum and CSF cytokine profiles and TNF-α levels of the test subjects or patients were measured. Clinical language rating scales such as (1) Childhood Autism Rating Scale and (2) Clinical Global Impression (CGI) were used to measure language and/or social skills. Autism diagnostic tests and CGI measures were used to measure behavioral improvement. Chemistry and hematology profiles were done periodically to assure safety.

According to the above conditions, four test subjects or patients diagnosed with an autism spectrum condition and with TNF-α CSF elevation over serum levels showed lowered levels of TNF-α in CSF and serum in 6 to 12 weeks; improved language and social skills; Childhood Autism Rating Scale Scores (CARS). Some patients with abnormal EEG showed improvement as well. The test subjects were administered dosages of lenalinomide of 2.5 mg per day.

The patients regressed in many of these skills with increased TNF-α levels in their serum levels after 4 to 12 weeks off the medication. This corresponded with some loss of skills gained in prior period of treatment. Three patients improved when medication was re-introduced at 2.5 to 5 mg per day.

Figure 1A:
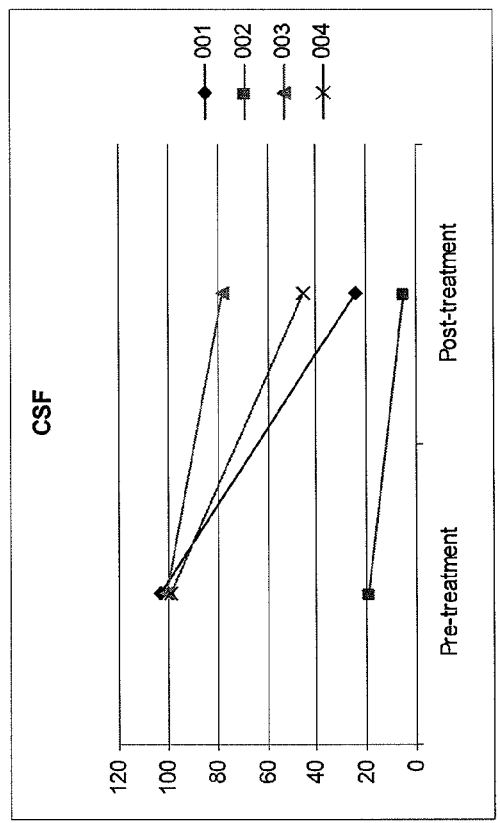
Figure 2B:
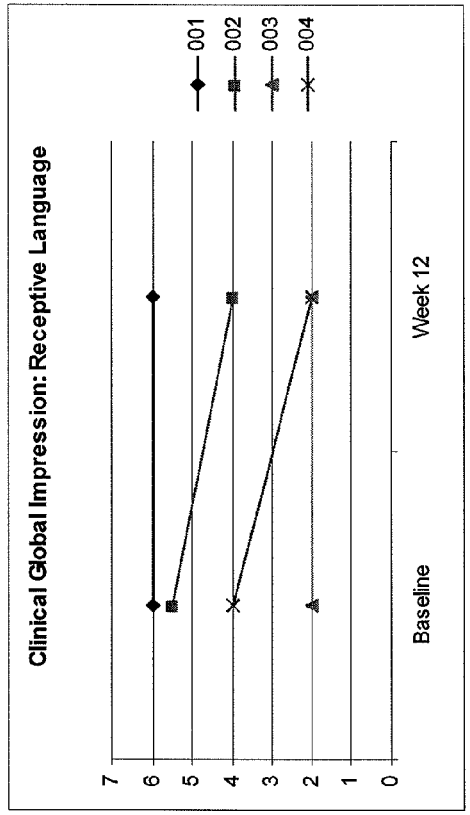
FIGS. 2a and 2b are graphs of Clinical Global Impression for Language Expressive and Receptive Language showing baseline and after treatment with lenalinomide.
Figure 2A:
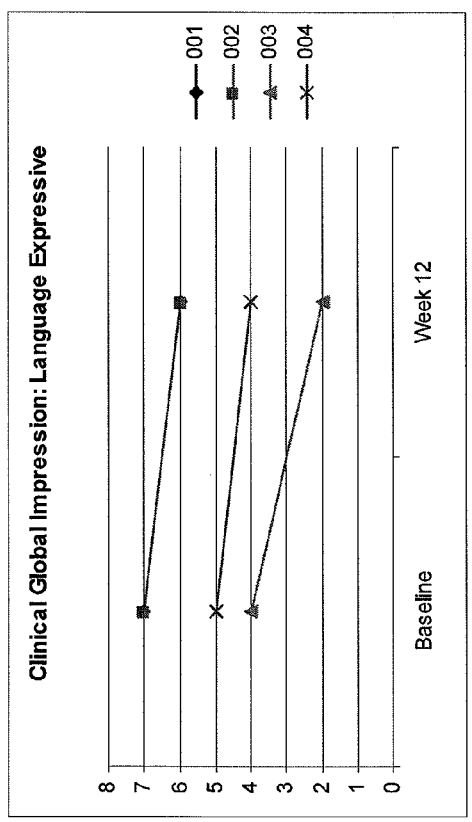
Figure 3:
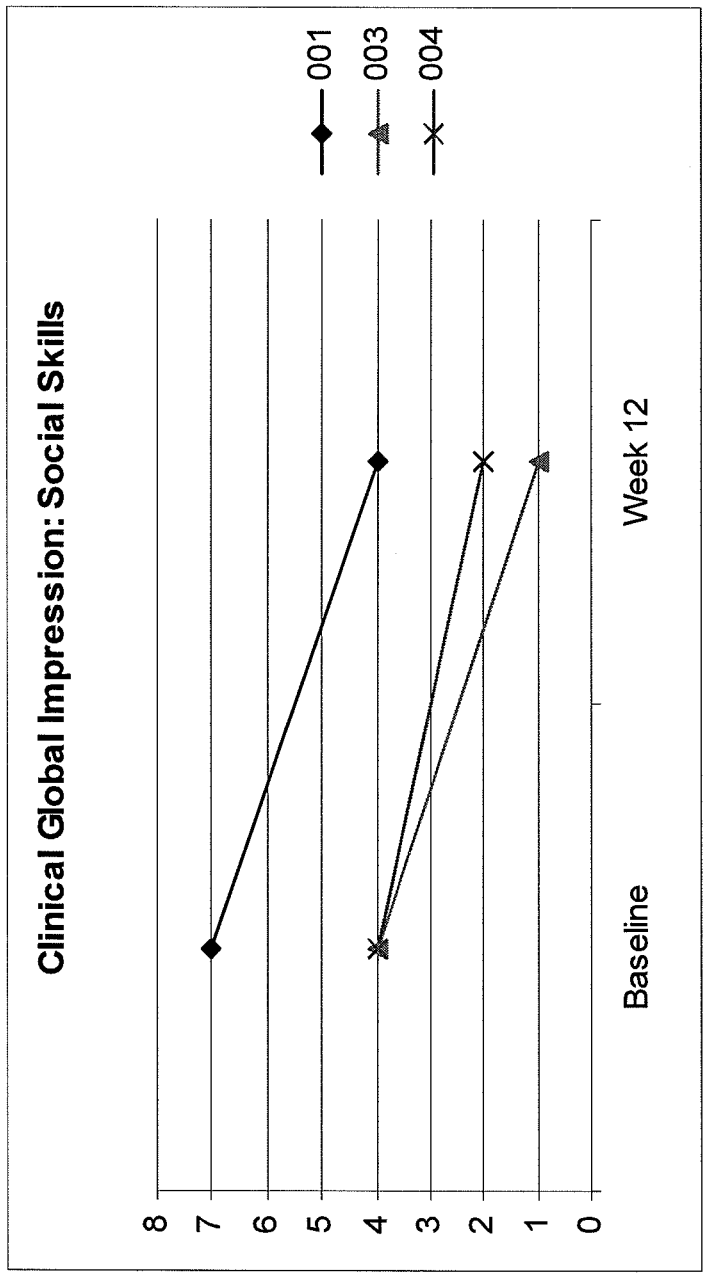
FIG. 3 is a graph of Clinical Global Impression for Social Skills showing baseline and after treatment with lenalinomide.
Figure 4A:
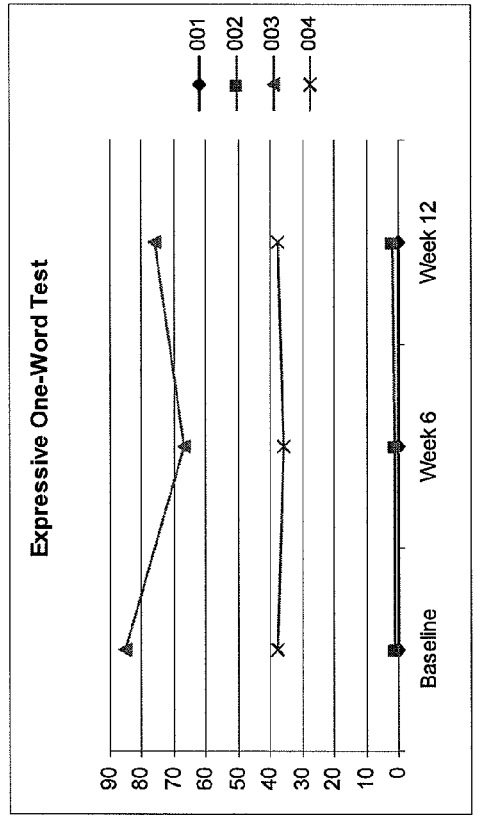
FIGS. 4a and 4b are graphs of Neuropsychological Testing (Receptive One-Word Test and Expressive One-Word Test) showing baseline and after treatment with lenalinomide.
Figure 4B:
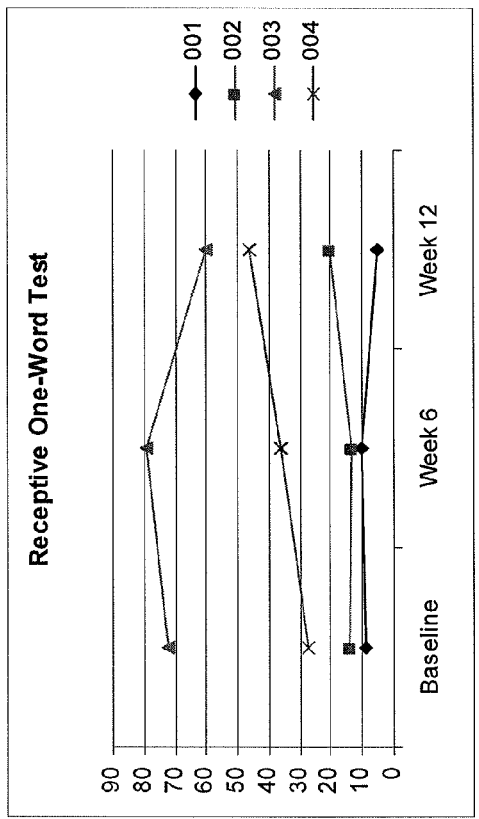
Figure 5:
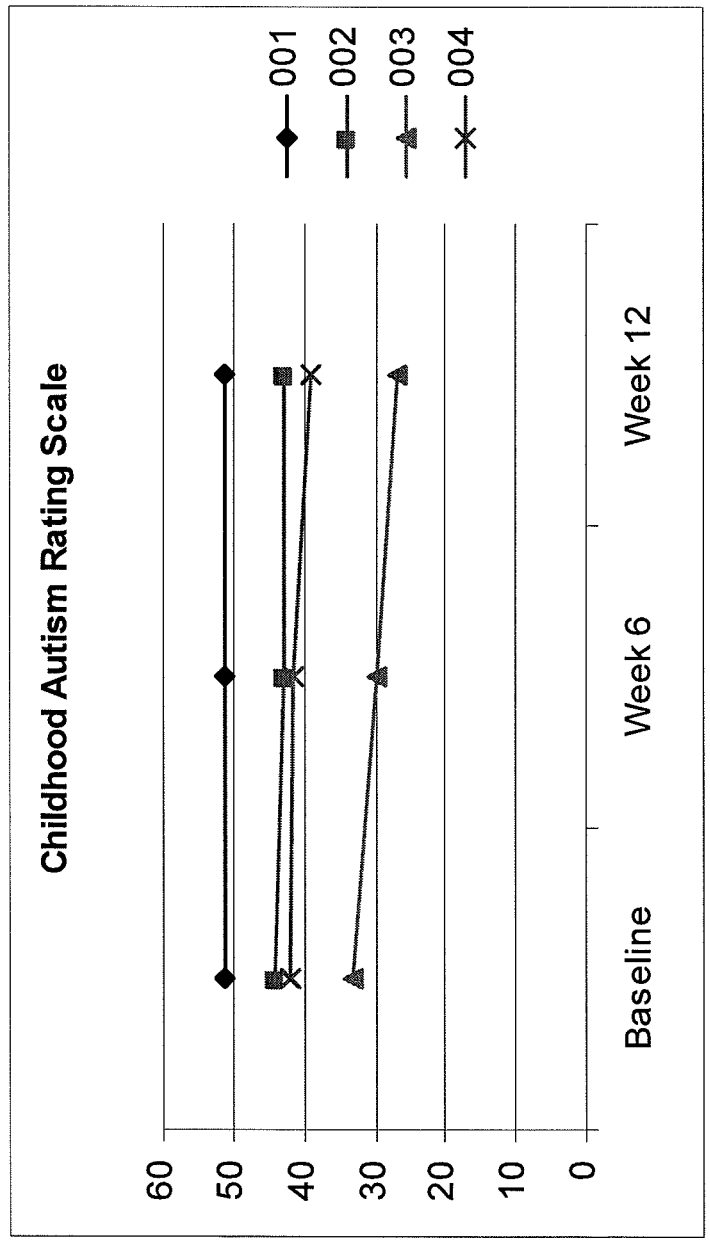
FIG. 5 is a graph of Neuropsychological Testing (CARS) showing baseline and after treatment with lenalinomide.

For test subjects or patients given 2.5 mg per day of lenalinomide, four out of four patients with elevated CSF TNF-α levels in CSF (FIG. 1a) and in serum (FIG. 1b) improved over baseline clinically (4/6 of completed study). Improvement in clinical language skills was shown by improvement in a CGI rating scale for language expression (FIG. 2a) and receptive language (FIG. 2b). Improvement in social skills was shown by improvement in a CGI rating scale, as shown in FIG. 3. Improvement in language skill was also observed via neuropsychological testing using a receptive one-word test (FIG. 4a) and expressive one-word test (FIG. 4b). Childhood Autism Rating Scale Scores (CARS) were observed as shown in FIG. 5. Additionally, EEG may have improved in 2 patients with abnormal EEG. Data suggest improvement based on treatment mechanism occurs in this population of autism with CSF/serum cytokine elevation.

Additionally, four subjects were treated with lenalinomide with dosages of 2.5 to 10 mg outside of above study and showed great clinical improvement and 2 subjects showed lower Interleukin-β levels as well in serum correlating to 12 to 24 weeks of therapy.

B. Thalidomide

Thalidomide or derivatives thereof have shown improvement in patients with autistic regression and abnormal EEG who previously showed immune partial response to oral or injectable corticosteroids.

In specific embodiments, clinical global improvement occurred and EEG improved using dosages of 25 to 50 mg thalidomide per day for 2 to 4 months in six patients.

C. L-Carnosine

L-Carnosine at dosages of 800 to 1000 mg to test subjects with autism spectrum condition showed language improvement and CARS scores improvement over 8 weeks. In specific embodiments, L-carnosine at 800 mg per day showed improvement in language function with receptive one word vocabulary testing scores after 6 and 12 weeks of treatment in autistic spectrum patients compared to placebo.

L-Carnosine with turmeric and/or Cat's Claw (for example, at dosages of 800 to 1000 mg l-carnosine with 500 mg turmeric and/or 500 mg Cat's Claw) showed clinically global improvement with CGI in areas of language and social function after 6 weeks.

In specific embodiments, these agents may be dietary supplements with anti-inflammatory properties which, among other mechanisms, particularly lower TNF-α levels.

D. Infliximab

Infliximab (REMICADE®) is an injectable treatment for autoimmune diseases and has been used in chronic inflammatory conditions of the gastrointestinal system.

In specific embodiments according to the present invention, a single patient with TNF-α elevation in serum over 10 times normal responded to treatment with infliximab. His co-morbid autism condition showed improvement in just days of treatment corresponding to lower TNF-α serum levels back to 1.5 normal or less. This patient regressed and became autistic after age 3 years with the onset of his inflammatory colitis condition becoming clinically obvious at a later date.

The examples of compounds above or similar derivatives have shown themselves clinically to lower TNF-α and, in autistic patients with elevated levels, have shown clinical responses in core areas of autism dysfunction including social and language areas. The earlier identification and treatment with these agents or similar compounds may offer more dramatic responses to the patients with identified TNF-α elevation who are earlier in their autism diagnosis.

This represents a unique mechanism of treatment for autism and pervasive developmental delay and similar conditions.

E. Additional Treatments

According to a specific embodiment, a patient may receive a 3 month therapy with corticosteroid (equivalent to 1-2 mg/kg per day prednisone) for immunomodulation followed by infusion of stem cells in form of mesenchymal or pluripotential infusion every 6 months for 3 doses of at least $1 \times 10^8$ cells.

According to a specific embodiment, a patient may be administered monthly stem cell infusions of $1 \times 10^6$ cells of at least one of pleuripotent, neuronally derived, or mesenchymal or immunoregulatory stem cell subtypes.

According to a specific embodiment, the use of a TNF-α alpha inhibitors such as thalidomide or lenalinomide orally every 3 days at doses 1-50 mg per day may be combined with carnosine 500-1000 mg daily for autism language improvement.

According to another embodiment of the present invention, pulse dose prednisone equivalent of 5-10 mg may be administered twice weekly with carnosine and/or another TNF-α inhibitor once weekly. In another embodiment, a patient may be administered weekly prednisone at 5 mg/kg per dose and weekly lenalinomide 10-50 mg/week or thalidomide 25-100 mg per week.

According to yet another specific embodiment, L-carnosine of 100 mg to 5000 mg per day plus turmeric or circumin of 100 to 1000 mg per day and cat's claw of 100 mg to 3000 mg per day in combination may be administered daily for anti-TNF and inflammatory affect also on interleukin-1β.

All of the above would work on language core symptoms and social improvement.

INDUSTRIAL APPLICABILITY

Methods and agents, such as medications or stem cell preparations, to reduce inflammatory markers in autism or pervasive developmental disorder patients having cerebrospinal fluid (CSF) and/or serum markers of cytokine inflammatory responses are provided.

Although specific embodiments of the invention have been described herein, it is understood by those skilled in the art that many other modifications and embodiments of the invention will come to mind to which the invention pertains, having benefit of the teaching presented in the foregoing description and associated drawings.

It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

REFERENCES

Chez M. G., Buchanan C., Loeffel M., Field-Chez M., Nowinski C. V., Bardenstein R., Hammer M. Practical treatment with pulse-dose corticosteroids in pervasive developmental delay or autistic patients with abnormal epileptiform sleep EEG and language delay. In: *New Developments in Child Neurology, Proceedings of the 8th World Congress of Child Neurology*. Perat M. V., ed. Bologna, Italy: Monduzzi Editore 1998. 695-698.

Chez, M. G., Aimonovich, M. C. Chapter VI: Carnosine in autistic spectrum disorders. Progress in Autism Research. Nova Science Publishers, Inc. Hauppage, N.Y. (2004): 219-228.

Chez, M. G., Chin, K., Hung, P. Immunizations, Immunology, and Autism. Seminars in Pediatric Neurology, 2004; 11 (3): 214-217.

Chez M. G., Buchanan C. P., Aimonovitch M. C., Becker M., Schaefer K, Black C., Komen J. Double-blind, placebo-controlled trial of l-carnosine supplementation in children with autistic spectrum disorders. *Journal of Child Neurology* 2002; 17(11):833-837

Chez, MG, Dowling, T, Patel, P, Khanna, P, Kominsky, M. Cerebrospinal fluid findings in autistic children with regression: evidence of localized elevation of tumor necrosis factor-alpha. Pediatric Neurology 2007; 36:361-365.

Vargas D L, Nascimbene C, Krishan C, Zimmerman A W, Pardo C A. Neuroglial activation and neuroinflammation in the brain of patients with autism. Ann Neurol 2005: 67-81

Zimmerman A, Jyonouchi H, Comi A, Connors S, Milstien S, Varsou A, Heyes M. Cerebrospinal fluid and serum markers of inflammation in autism. Pediatr Neurol, 2005:195-201

Connelly, A M, Chez M G, Pestronk A, Arnold, S T, Mehta, S, Deuel, R K: Serum autoantibodies to brain in Landau-Kleffner variant, autism, and other neurologic disorders. J Pediatr 1999:607-613.

What is claimed is:

1. A method for treating an autism spectrum disorder or pervasive development disorder, comprising:
    administering an effective dose of a TNF-α inhibiting agent to a person having an autism spectrum disorder or pervasive development disorder and an elevated ratio of TNF-α in the cerebrospinal fluid to TNF-α in serum; and
    lowering the elevated ratio of TNF-α in the cerebrospinal fluid to TNF-α in the serum,
    wherein the TNF-α inhibiting agent is selected from the group consisting of lenalinomide; thalidomide; l-carnosine; infliximab; etanercept; and derivatives, isomers, or pharmaceutically acceptable salts of the TNF-α inhibiting agent.

2. A method according to claim 1 wherein said administering an effective dose of a TNF-α inhibiting agent to a person having an autism spectrum disorder or pervasive development disorder lowers levels of a proinflammtory cytokine.

3. A method according to claim 2, wherein the proinflammatory cytokine comprises interleukin-1β.

4. A method according to claim 1, wherein the TNF-α inhibiting agent comprises lenalinomide.

5. A method according to claim 1, wherein the person is a male less than 16 years of age.

6. A method according to claim 1, further comprising administering a corticosteroid to said person.

7. A method according to claim 1, wherein autism spectrum disorder or pervasive development disorder comprises autism or Asperger's.

8. A method according to claim 1, further comprising measuring language skills or social skills of the person.

9. A method for treating an autism spectrum disorder or pervasive development disorder, comprising:
    administering an effective dose of a TNF-α inhibiting agent to a patient having an autism spectrum disorder or pervasive development disorder and having an elevated ratio of TNF-α in the cerebrospinal fluid to TNF-α in serum;

lowering the elevated ratio of TNF-α in the cerebrospinal fluid to TNF-α in the serum; and lowering a serum level of a cytokine, wherein the TNF-α inhibiting agent is selected from the group consisting of lenalinomide; thalidomide; I-carnosine; infliximab; etanercept; and derivatives, isomers, or pharmaceutically acceptable salts of the TNF-α inhibiting agent.

10. A method according to claim 9, further comprising measuring language skills or social skills of the patient.

11. A method according to claim 9, wherein the cytokine marker comprises Interleuken-1β.

* * * * *